United States Patent [19]

Finley et al.

[11] 4,207,070
[45] Jun. 10, 1980

[54] PEROXYGEN BLEACHING AND COMPOSITIONS THEREFOR

[75] Inventors: Joseph H. Finley, Metuchen; Gaylen R. Brubaker, Lawrenceville; Burton M. Baum, Princeton, all of N.J.

[73] Assignee: FMC Corporation, Philadelphia, Pa.

[21] Appl. No.: 949,836

[22] Filed: Oct. 10, 1978

[51] Int. Cl.$^2$ .......................... D06L 3/02; D06L 3/04
[52] U.S. Cl. .......................................... 8/111; 252/95; 252/99; 252/186
[58] Field of Search ................ 8/111; 252/95, 99, 186

[56] References Cited

U.S. PATENT DOCUMENTS

| | | | |
|---|---|---|---|
| 2,284,477 | 5/1942 | Reichert et al. | 260/502 |
| 2,955,905 | 10/1960 | Davies et al. | 8/111 |
| 3,298,775 | 1/1967 | Malafosse et al. | 8/101 |
| 3,321,497 | 5/1967 | Matzner | 260/397.7 |
| 3,532,634 | 10/1970 | Woods | 252/95 |
| 3,706,670 | 12/1972 | Gray | 252/95 |
| 3,775,333 | 11/1973 | Loffelman | 252/99 |
| 3,886,078 | 5/1975 | Loffelman | 252/102 |
| 3,912,648 | 10/1975 | Brady et al. | 252/102 |
| 3,919,102 | 11/1975 | Kuhling | 252/99 |
| 3,969,257 | 7/1976 | Murray | 252/102 |
| 4,115,060 | 9/1978 | Finley et al. | 8/111 |

FOREIGN PATENT DOCUMENTS 1802015 10/1968 Fed. Rep. of Germany .
48-90980 11/1973 Japan .
1242287 8/1971 United Kingdom .

*Primary Examiner*—Melvyn I. Marquis
*Attorney, Agent, or Firm*—Robert D. Jackson; Frank Ianno

[57] ABSTRACT

A process of removing soil and/or stains from fabrics by immersing the fabrics in a peroxygen bleach bath containing as a peroxygen activator a N-sulfonylazole of the formula

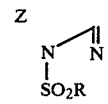

where Z represents the number of carbon and nitrogen atoms necessary to complete a heterocyclic ring selected from the class consisting of pyrazole, pyrrole, triazole, and benzotriazole wherein said ring can be substituted with phenyl, alkyl of 1 to 10 carbon atoms, halogen, amino, cyano, nitro, alkoxy of 1 to 10 carbon atoms and R is an alkyl radical of 1 to 10 carbon atoms.

Also described are dry blend compositions containing the bleach bath components.

6 Claims, No Drawings

PEROXYGEN BLEACHING AND COMPOSITIONS THEREFOR

This invention relates to active oxygen compositions. In particular, the invention is concerned with activated peroxygen compounds and their application to laundering operations.

The use of bleaching agents as laundering aids is well known. In fact, such entities are considered necessary ajuncts for cleaning today's fabrics which embrace a wide spectrum of synthetic, natural and modified natural fiber systems, each differing in washing characteristics.

Laundry bleaches generally fall into one of two categories; active oxygen-releasing or peroxygen and active chlorine-releasing. Of the two, the chlorine bleach is more likely to react with the various components of a detergent washing formulation than peroxygen bleaches. Moreover, fabrics treated with chlorine bleaches exhibit significant loss of strength and depending on the frequency of bleaching, the useful life of the cloth may be appreciably reduced; with dyed fabrics, colors are often degraded. Another objection to chlorine bleaches is their pronounced tendency to cause yellowing, particularly with synthetics and resin treated fabrics. Peroxygen bleaches are substantially free of such adverse side effects.

Despite their many advantages, bleaching agents of the active oxygen-releasing type are as a class not optimally effective until use temperatures exceed about 85° C., usually 90° C., or higher. This rather critical temperature-dependency of peroxygen bleaching agents and especially the persalt bleaches such as sodium perborate poses a rather serious drawback since many household washing machines are now being operated at water temperatures less than about 60° C., well below those necessary to render bleaching agents such as the perborates adequately effective. Although the near boiling washing temperatures employed in Europe and some other countries favor the use of peroxygen bleaches, it can be expected that such temperatures will be lowered in the interest of conserving energy. Consequently, where a comparatively high order of bleaching activity at reduced temperature is desired, resort must be had to chlorine bleaches despite their attendant disadvantages, that is, impairment of fabric strength, fabric discoloration, and the like.

In an effort to realize the full potential of peroxygen bleaches, such materials have been the focus of considerable research and development effort over the years. One result of these investigations was the finding that certain substances, activators as they are usually called, have the capacity of amplifying the bleaching power of peroxygen compounds below about 60° C. where many home washing machines are commonly operated, or preferably operated. Although the precise mechanism of peroxygen bleach activation is not known, it is believed that activator-peroxygen interaction leads to the formation of an intermediate species which constitutes the active bleaching entity. In a sense, then, the activator-peroxygen component functions as a precursor system by which the in place generation of species providing effective bleaching means is made possible.

Although numerous compounds have been proposed and tested as peroxygen bleach activators, a satisfactory candidate has thus far not been forthcoming. Perhaps the primary objection is the failure to provide the desired degree of bleaching activity within the limitations imposed by economically feasible practice. Thus, it is often necessary to utilize the activator compound in inordinately high concentrations in order to achieve satisfactory results; in other instances, it is found that a given activator is not generally applicable and thus may be used advantageously only in conjunction with rather specific and delimited types of peroxygen bleaching agents. Other disadvantages characterizing many of the activator compounds thus far contemplated include, for example, the difficulties associated with their incorporation into detergent powder compositions including stability problems and short shelf life.

Representative prior art activators for peroxygen bleaches include carboxylic acid anhydrides disclosed in U.S. Pat. Nos. 2,284,477, 3,532,634 and 3,298,775; carboxylic esters disclosed in U.S. Pat. No. 2,955,905; N-substituted, N-acylnitrobenzenesulfonamides disclosed in U.S. Pat. No. 3,321,497; N-benzoylsaccharin disclosed in U.S. Pat. No. 3,886,078; N-acyl compounds such as those described in U.S. Pat. Nos. 3,912,648 and 3,919,102 and aromatic sulfonyl chlorides disclosed in Japanese Patent Publication No. 90980 of November 27, 1973; N-sulfonylimides are disclosed in Offenlegungsschrift 1,802,015 published June 19, 1969; N-acylazolinones are described in U.S. Pat. No. 3,775,333; phosphoric-carboxylic anhydrides disclosed in British Pat. No. 925,725 and phosphonic-carboxylic and phosphinic-carboxylic anhydrides disclosed in British Pat. No. 1,059,434.

While certain of these activators are effective in varying degrees, there is a continuing need for candidate compounds of improved performance and properties.

One promising class of peroxygen activators is the N-acylazoles described in U.S. Pat. No. 3,816,324 and identified by the formulae:

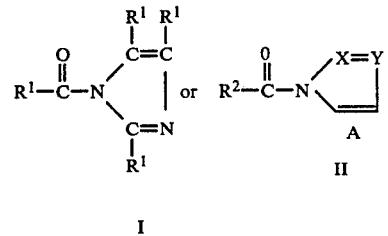

wherein $R^1$ is hydrogen, alkyl, halogen or nitro; $R^2$ is a substituted or unsubstituted alkyl, alicyclic or aryl radical; A is a mono- or disubstituted or unsubstituted 6-membered aromatic or N-heteroaromatic ring having 1–4 nitrogen atoms; and X and Y are nitrogen and $C-R^1$, and at least one of X and Y is nitrogen.

However, it was found that peroxygen bleach compositions containing such compounds, while initially effective, tend to deteriorate during storage with concomitant loss of potency. Apparently, the N-acyl group is subject to hydrolytic clevage, since loss of bleaching power is aggravated under conditions of high humidity. Analysis of the aged compositions reveals the presence of peroxycarboxylic acid, presumably formed from the eliminated N-acyl function. Moreover, the stored compositions give off the characteristic acid odor of a peroxycarboxylic acid. From the foregoing, it is evident that the N-acylazoles are not a satisfactory type of activator, at least from a practical standpoint.

An improved class of N-substituted azole peroxygen activators are the N-sulfonylimadiazoles described in our copending application Ser. No. 839,067, filed Oct. 3, 1977. These compounds are superior to the aforedescribed N-acylazoles in that peroxygen bleach compositions prepared therefrom have excellent storage stability.

According to the process of the present invention the bleaching capacity of peroxygen bleaches is increased by contacting them with an N-sulfonylazole wherein the azole contains a pyrazole, a pyrrole, or a triazole ring. There are provided bleaching compositions containing such components which are used alone or in conjunction with conventional laundering processes and materials to treat soiled and/or stained fabrics.

So far as can be ascertained, the N-sulfonylazoles of the invention are, as a class, effective activators for peroxygen bleaching agents. Of course, the type and size of substituents attached to the azole ring or N-sulfonyl function will influence the degree of activation. Thus, where the substituent consists of a bulky hydrocarbon or heterocyclic moiety, the resulting N-sulfonylazole may be too insoluble to exhibit peroxygen activation. On the other hand, such insolubility can be mitigated by introducing into the molecule a soluble salt forming group as exemplified by $SO_3H$ or COOH. Other substituents such as $NO_2$, Cl, Br, alkoxyl, amino, and cyano will affect solubility and other physical properties in varying degrees; polyvalent radicals such as —O— or —N lower alkyl— can be interpolated in an alkyl chain as another measure to control solubility. The number of substituents as well as the size and type must not mask or overcome the functionality of the sulfonyl group. In the interest of economy, the substituents will be hydrocarbon radicals having minimal groups attached thereto and free of complex branching. Once a person skilled in the art is made aware of the peroxygen activating properties of the herein N-sulfonylazoles, he will know not to select inoperative members of the class.

Generally speaking, the N-sulfonylazoles of the present invention can be depicted by the following formula:

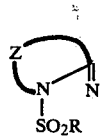

wherein Z represents the number of carbon and nitrogen atoms necessary to complete a heterocyclic ring selected from the class consisting of pyrazole, pyrrole, triazole, and benzotriazole wherein said ring can be substituted with phenyl, alkyl of 1 to 10 carbon atoms and R is an alkyl radical of 1 to 10 carbon atoms or an aromatic hydrocarbon radical of 6 to 10 carbon atoms.

The N-sulfonylazoles constitute a known class of chemical entities, representative members of which are disclosed in the technical literature. They can be prepared by reacting the requisite sulfonyl halide with the appropriate azole in accordance with the following scheme:

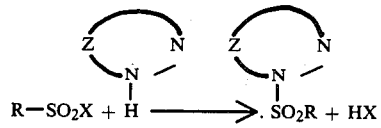

wherein Z and R are typically as above defined and X is preferably chlorine.

Generally, the reaction is carried out in the presence of an acid binding agent which neutralizes the HX. Any base of the type commonly known as an acid binding agent can be used. Suitable bases include alkali metal salts of weak acids such as sodium acetate and tertiary organic amines such as pyridine and trialkylamines, preferably triethylamine. The reaction is conveniently carried out in a liquid media, preferably a normally liquid, relatively inert organic solvent. Representative solvents are ethers and halogenated hydrocarbons. The sulfonylazole product generally separates from the reaction mixture as a solid which can be purified in the known manner such as crystallization. Where the H of the azole is feebly acidic, the sodium salt of the azole is used. The latter can be obtained by reacting the azole with sodium hydride.

Exemplary N-sulfonylazoles falling within the ambit of the description aforesaid include:
1-(p-Tolylsulfonyl)pyrazole
1-[(4-Methylphenyl)sulfonyl]-5-nitro-1H-benzotriazole
1-(Phenylsulfonyl)-1H-1,2,4-triazole
1-(p-Tolylsulfonyl)-1H-1,2,4-triazole
1-(Phenylsulfonyl)-3-propyl-1H-1,2,4-triazole
1-(2,3,-Xylysulfonyl)-1H-1,2,4-triazole
5-Methyl-1-(p-Tolylsulfonyl)-1H-1,2,3-triazole
3-Amino-5-(naphthyloxy)-1-(phenylsulfonyl) 1H-1,2,4-triazole
5-Amino-1-(phenylsulfonyl)-3-(p-tolyloxy)-1H-1,2,4-triazole
1-[(p-Methoxyphenyl)sulfonyl]-3,5-dimethyl-1H-1,2,4-triazole
1-(Benzylsulfonyl)-3,5-dimethylpyrazole
1-[(3,5-Dimethyl-4-oxazolyl)sulfonyl]-3,5-dimethylpyrazole In accordance with the invention, low temperature bleaching (that is, below about 60° C.) of stained and/or soiled fabrics is effected by contacting them with a solution containing a N-sulfonylazole activator herein and an active oxygen-releasing compound. The active oxygen-releasing compounds include such peroxygen compounds as hydrogen peroxide or those peroxygen compounds that liberate hydrogen peroxide in aqueous media. Examples of such peroxygen compounds are urea peroxide, alkali metal perborates, percarbonates, perphosphates, persulfates, monopersulfates and the like. Combinations of two or more peroxygen bleaches can be used where desired. The same holds true in the case of the activators. Although any number of peroxygen compounds are suitable in carrying out the invention, a preferred compound is sodium perborate tetrahydrate, since it is a readily available commercial product. Another suitable persalt is sodium carbonate peroxide.

Sufficient peroxygen compounds to provide from about 2 parts per million to 2,000 parts per million active oxygen in solution are used. For home bleaching applications, the concentration of active oxygen in the wash water is desirably from about 5 to 100 parts per million, preferably about 15 to 60 parts per million. Sodium perborate tetrahydrate, the preferred peroxygen compound, contains 10.4% active oxygen. The actual concentration employed in a given bleaching solution can be varied widely, depending on the intended use of the solution.

The concentration of the N-sulfonylazole in the bleaching solution depends to a large extent on the concentration of the peroxygen compound which, in turn, depends on the particular use for which a given composition is formulated. Higher or lower levels can be selected according to the needs of the formulator. Overall, increased bleaching results are realized when the active oxygen of the peroxygen compound and N-sulfonylazole are present in a mole ratio in the range of from about 20:1 to 1:3, preferably from about 10:1 to 1:1.

Activation of the peroxygen bleaches is generally carried out in aqueous solution at a pH of from about 6 to about 12, most preferably 8.0 to 10.5. Since an aqueous solution of persalts or peracids is generally acidic, it is necessary to maintain the requisite pH conditions by means of buffering agents. Buffering agents suitable for use herein include any non-interfering compound which can alter and/or maintain the solution pH within the desired range, and the selection of such buffers can be made by referring to a standard text.

For instance, phosphates, carbonates, or bicarbonates, which buffer within the pH range of 6 to 12 are useful. Examples of suitable buffering agents include sodium bicarbonate, sodium carbonate, sodium silicate, disodium hydrogen phosphate, sodium dihydrogen phosphate. The bleach solution may also contain a detergent agent where bleaching and laundering of the fabric is carried out simultaneously. The strength of the detergent agent is commonly about 0.05% to 0.80% (wt.) in the wash water.

Although the activator, buffer and peroxygen compound can be employed individually in formulating the bleach solutions of the invention, it is generally more convenient to prepare a dry blend of these components and the resulting composition added to water to produce the bleach solution. A soap or organic detergent can be incorporated into the composition to give a solution having both washing and bleaching properties. Organic detergents suitable for use in accordance with the present invention encompass a relatively wide range of materials and may be of the anionic, non-ionic, cationic or amphoteric types.

The anionic surface active agents include those surface active or detergent compounds which contain an organic hydrophobic group and an anionic solubilizing group. Typical examples of anionic solubilizing groups are sulfonate, sulfate, carboxylate, phosphonate and phosphate. Examples of suitable anionic detergents which fall within the scope of the invention include the soaps, such as the water-soluble salts of higher fatty acids or rosin acids, such as may be derived from fats, oils, and waxes of animal, vegetable or marine origin, for example, the sodium soaps of tallow, grease, coconut oil, tall oil and mixtures thereof; and the sulfated and sulfonated synthetic detergents, particularly those having about 8 to 26, and preferably about 12 to 22, carbon atoms to the molecule.

As examples of suitable synthetic anionic detergents the higher alkyl mononuclear aromatic sulfonates are preferred particularly the LAS type such as the higher alkyl benzene sulfonates containing from 10 to 16 carbon atoms in the alkyl group, for example, the sodium salts such as decyl, undecyl, dodecyl (lauryl), tridecyl, tetradecyl, pentadecyl, or hexadecyl benzene sulfonate and the higher alkyl toluene, xylene and phenol sulfonates; alkyl naphthalene sulfonate, ammonium diamyl naphthalene sulfonate, and sodium dinonyl naphthalene sulfonate.

Other anionic detergents are the olefin sulfonates including long chain alkene sulfonates, long chain hydroxyalkane sulfonates or mixtures of alkenesulfonates and hydroxyalkanesulfonates. These olefin sulfonate detergents may be prepared, in known manner, by the reaction of $SO_3$ with long chain olefins (of 8-25 preferably 12-21 carbon atoms) of the formula $RCH\text{-}CHR^1$, where R is alkyl and $R^1$ is alkyl or hydrogen, to produce a mixture of sultones and alkenesulfonic acids, which mixture is then treated to convert the sultones to sulfonates. Examples of other sulfate or sulfonate detergents are paraffin sulfonates, such as the reaction products of alpha olefins and bisulfites (for example, sodium bisulfite), for example, primary paraffin sulfonates of about 10-20 preferably about 15-20 carbon atoms; sulfates of higher alcohols; salts of $\alpha$-sulfofatty esters for example of about 10 to 20 carbon atoms, such as methyl $\alpha$-sulfomyristate or $\alpha$-sulfotallowate).

Examples of sulfates of higher alcohols are sodium lauryl sulfate, sodium tallow alcohol sulfate; Turkey Red Oil or other sulfated oils, or sulfates of mono- or diglycerides of fatty acids (for example, stearic monoglyceride monosulfate), alkyl poly(ethenoxy) ether sulfates such as the sulfates of the condensation products of ethylene oxide and lauryl alcohol (usually having 1 to 5 ethenoxy groups per molecule); lauryl or other higher alkyl glyceryl ether sulfonates; aromatic poly(ethenoxy) ether sulfates such as the sulfates of the condensation products of ethylene oxide and nonyl phenol (usually having 1 to 20 oxyethylene groups per molecule, preferably 2-12).

The suitable anionic detergents include also the acyl sarcosinates (for example, sodium lauroylsarcosinate) the acyl ester (for example, oleic acid ester) of isethionates, and the acyl N-methyl taurides (for example, potassium N-methyl lauroyl or oleyl tauride).

Other highly preferred water soluble anionic detergent compounds are the ammonium and substituted ammonium (such as mono-, di- and triethanolamine), alkali metal (such as sodium and potassium) and alkaline earth metal (such as calcium and magnesium) salts of the higher alkyl sulfates, and the higher fatty acid monoglyceride sulfates. The particular salt will be suitably selected depending upon the particular formulation and the proportions therein.

Nonionic surface active agents include those surface active or detergent compounds which contain an organic hydrophobic group and a hydrophilic group which is a reaction product of a solubilizing group such as carboxylate, hydroxyl, amido or amino with ethylene oxide or with the polyhydration product thereof, polyethylene glycol.

As examples of nonionic surface active agents which may be used there may be noted the condensation products of alkyl phenols with ethylene oxide, for example, the reaction product of octyl phenol with about 6 to 30 ethylene oxide units; condensation products of alkyl thiophenols with 10 to 15 ethylene oxide units; condensation products of higher fatty alcohols such as tridecyl alcohol with ethylene oxide; ethylene oxide addends of monoesters of hexahydric alcohols and inner ethers thereof such as sorbitol monolaurate, sorbitol mono-oleate and mannitol monopalmitate, and the condensation products of polypropylene glycol with ethylene oxide.

Cationic surface active agents may also be employed. Such agents are those surface active detergent compounds which contain an organic hydrophobic group and a cationic solubilizing group. Typical cationic solubilizing groups are amine and quaternary groups.

As examples of suitable synthetic cationic detergents there may be noted the diamines such as those of the type $RNHC_2H_4NH_2$ wherein R is an alkyl group of about 12 to 22 carbon atoms, such as N-2-aminoethyl stearyl amine and N-2-aminoethyl myristyl amine; amide-linked amines such as those of the type $R^1CONHC_2H_4NH_2$ wherein R is an alkyl group of about 9 to 20 carbon atoms, such as N-2-amino ethyl stearyl amide and N-amino ethyl myristyl amide; quaternary ammonium compounds wherein typically one of the groups linked to the nitrogen atom are alkyl groups which contain 1 to 3 carbon atoms, including such 1 to 3 carbon alkyl groups bearing inert substituents, such as phenyl groups, and there is present an anion such as halide, acetate, methosulfate, and the like. Typical quaternary ammonium detergents are ethyl-dimethyl-stearyl ammonium chloride, benzyl-dimethyl-stearyl ammonium chloride, benzyl-diethyl-stearyl ammonium chloride, trimethyl stearyl ammonium chloride, trimethyl-cetyl ammonium bromide, dimethylethyl dilauryl ammonium chloride, dimethyl-propyl-myristyl ammonium chloride, and the corresponding methosulfates and acetates.

Examples of suitable amphoteric detergents are those containing both an anionic and a cationic group and a hydrophobic organic group, which is advantageously a higher aliphatic radical, for example, of 10–20 carbon atoms. Among these are the N-long chain alkyl amino-carboxylic acids for example of the formula

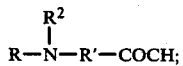

the N-long chain alkyl iminodicarboxylic acids (for example of the formula $RN(R'COOH)_2$) and the N-long chain alkyl betaines for example of the formula

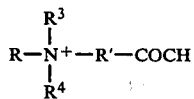

where R is a long chain alkyl group, for example of about 10–20 carbons, R' is a divalent radical joining the amino and carboxyl portions of an amino acid (for example, an alkylene radical of 1–4 carbon atoms), H is hydrogen or a salt-forming metal, $R^2$ is a hydrogen or another monovalent substituent (for example, methyl or other lower alkyl), and $R^3$ and $R^4$ are monovalent substituents joined to the nitrogen by carbon-to-nitrogen bonds (for example, methyl or other lower alkyl substituents). Examples of specific amphoteric detergents are N-alkyl-beta-aminopropionic acid; N-alkyl-betaiminodipropionic acid, and N-alkyl, N,N-dimethyl glycine; the alkyl group may be, for example, that derived from coco fatty alcohol, lauryl alcohol, myristyl alcohol (or a lauryl-myristyl mixture), hydrogenated tallow alcohol, cetyl, stearyl, or blends of such alcohols. The substituted aminopropionic and iminodipropionic acids are often supplied in the sodium or other salt forms, which may likewise be used in the practice of this invention. Examples of other amphoteric detergents are the fatty imidazolines such as those made by reacting a long chain fatty acid (for example of 10 to 20 carbon atoms) with diethylene triamine and monohalo-carboxylic acids having 2 to 6 carbon atoms, for example, 1-coco-5-hydroxyethyl-5-carboxymethylimidazoline; betaines containing a sulfonic group instead of the carboxylic group; betaines in which the long chain substituent is joined to the carboxylic group without an intervening nitrogen atom, for example, inner salts of 2-trimethylamino fatty acids such as 2-trimethylaminolauric acid, and compounds of any of the previously mentioned types but in which the nitrogen atom is replaced by phosphorus.

The instant compositions optionally contain a detergency builder of the type commonly added to detergent formulations. Useful builders herein include any of the conventional inorganic and organic water-soluble builder salts. Inorganic detergency builders useful herein include, for example, water-soluble salts of phosphates, pyrophosphates, orthophosphates, polyphosphates, silicates, carbonates, zeolites, including natural and synthetic and the like. Organic builders include various water-soluble phosphonates, polyphosphonates, polyhydroxysulfonates, polyacetates, carboxylates, polycarboxylates, succinates, and the like.

Specific examples of inorganic phosphate builders include sodium and potassium tripolyphosphates, phosphates, and hexametaphosphates. The organic polyphosphonates specifically include, for example, the sodium and potassium salts of ethane 1-hydroxy-1,1-diphosphonic acid and the sodium and potassium salts of ethane-1,1,2-triphosphonic acid. Examples of these and other phosphorus builder compounds are disclosed in U.S. Pat. Nos. 3,159,581, 3,213,030, 3,422,021, 3,422,137, 3,400,176 and 3,400,148. Sodium tripolyphosphate is an especially preferred, water-soluble inorganic builder herein.

Non-phosphorus containing sequestrants can also be selected for use herein as detergency builders.

Specific examples of non-phosphorus, inorganic builder ingredients include water-soluble inorganic carbonate, bicarbonate, and silicate salts. The alkali metal, for example, sodium and potassium, carbonates, bicarbonates, and silicates are particularly useful herein.

Water-soluble, organic builders are also useful herein. For example, the alkali metal, ammonium and substituted ammonium polyacetates, carboxylates, polycarboxylates and polyhydroxysulfonates are useful builders in the present compositions and processes. Specific examples of the polyacetate and polycarboxylate builder salts include sodium, potassium, lithium, ammonium and substituted ammonium salts of ethylenediaminetetraacetic acid, nitrilotriacetic acid, oxydisuccinic acid, mellitic acid, benzene polycarboxylic (that is, penta- and tetra-) acids, carboxymethoxysuccinic acid and citric acid.

Highly preferred non-phosphorus builder materials (both organic and inorganic) herein include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Other preferred organic builders herein are the polycarboxylate builders set forth in U.S. Pat. No. 3,308,067.

Examples of such materials include the water-soluble salts of homo- and copolymers of aliphatic carboxylic acids such as maleic acid, itaconic acid, mesaconic acid, fumaric acid, aconitic acid, citraconic acid and methylenemalonic acid.

The builders aforesaid, particularly the inorganic types, can function as buffers to provide the requisite alkalinity for the bleaching solution. Where the builder does not exhibit such buffer activity, an alkaline reacting salt can be incorporated in the formulation.

The compositions of the invention contain about 0.1 to 50% (wt.), preferably 0.5 to 20% (wt.) of the herein N-sulfonylazole activator. It will be appreciated that the concentration of activator will depend on the concentration of the peroxygen bleach compound which is governed by the particular degree of bleaching desired. Higher or lower levels within the range will be selected to meet the requirement of the formulator. As to the peroxygen bleaching agent, this is present to the extent of about 1 to 75% (wt.) of the composition, depending on the degree of bleaching activity desired. Generally speaking, optimal bleaching is obtained when the compositions are formulated with a peroxygen/sulfonylazole mole ratio in the range of from about 20:1 to 1:3, preferably about 10:1 to about 1:1. The composition will contain a buffering agent in sufficient quantity to maintain a pH of about 6 to 12 when the composition is dissolved in water. The buffering agent can constitute from about 1% to about 95% (wt.) of the dry blended composition.

The herein activated bleach compositions can be provided for use in combination with a detergent agent or as a fully-formulated built detergent. Such compositions will comprise from about 5 to 50% of the activated bleach system, from about 5 to 50% (wt.) of the detergent agent and optionally from about 1 to 60% (wt.) of a detergency builder which can also function as a buffer to provide the requisite pH range when the composition is added to water.

The compositions herein can include detergent adjunct materials and carriers commonly found in laundering and cleaning compositions. For example, various perfumes, optical brighteners, fillers, anti-caking agents, fabric softeners, and the like can be present to provide the usual benefits occasioned by the use of such materials in detergent compositions. Enzymes, especially the thermally stable proteolytic and lipolytic enzymes used in laundry detergents, also can be dry-mixed in the compositions herein.

The solid peroxygen bleaching compositions herein are prepared by simply admixing the ingredients. When preparing mixed detergent/bleaches, the peroxygen and activator can be mixed either directly with the detergent compound, builder, and the like, or the peroxygen and activator can be separately or collectively coated with a water-soluble coating material to prevent premature activation of the bleaching agent. The coating process is conducted according to known procedures in the art utilizing known coating materials. Suitable coating materials include compounds such as magnesium sulfate hydrate, polyvinyl alcohol, or the like.

Evaluation of Compounds as Bleach Activators

Compounds of the invention were evaluated for bleach activating efficacy by determining the increase in percent tea stain removal (%TSR) achieved by use of both the peroxygen source and activator compared with that obtained by use of the peroxygen source alone. Both tests were performed under otherwise identical low temperature laundering conditions. The increase in %TSR is called Δ%TSR. The evaluation was carried out in the presence of a detergent formulation and sodium perborate tetrahydrate as the source of peroxygen compound.

Tea-stained cotton and 65% dacron/35% cotton swatches 10.2×12.7 cm. (4"×5") used in these tests were prepared as follows: For each 50 swatches, 2000 ml of tap water was heated to boiling in a four-liter beaker. Reflectance readings were made on each swatch, using a Hunter Model D-40 Reflectometer before staining. Two family size tea bags were added to each beaker and boiling was continued for five minutes. The tea bags were then removed and 50 fabric swatches were added to each beaker. The dacron/cotton and 100% cotton swatches were boiled in the tea solution for five minutes after which the entire content of each beaker was transferred to a centrifuge and rotated for about 0.5 minutes.

The swatches were then dried for thirty minutes in a standard household laundry drier. One hundred dry swatches were rinsed four times by agitating manually in 2000 ml portions of cold tap water. The swatches were dried in the household drier for approximately 40 minutes; they were allowed to age for at least three days before use. Reflectance readings for each swatch were taken prior to bleaching tests, using a Hunter Model D-40 Reflectometer.

Three stained cotton and polyester/cotton swatches were added to each of several stainless steel Terg-O-Tometer vessels containing 1000 ml of 0.15% detergent solution, maintained at a constant temperature of 40° C. The Terg-O-Tometer is a test washing device manufactured by the U.S. Testing Company. The detergent solution was prepared from a detergent formulation having the following composition (by weight):

25.0% - Sodium tripolyphosphate
7.5% - Sodium dodecylbenzenesulfonate (anionic surfactant)
4.0% - Alcohol ether sulfate (obtained from 1 mole of $C_{16}$–$C_{18}$ alcohol with 1 mole ethylene oxide (anionic surfactant)
6.5% - Alcohol ($C_{16}$–$C_{18}$) sulfate (anionic surfactant)
1.3% - Polyethylene glycol of about 6000 molecular wt.
35.4% - Sodium sulfate
11.0% - Sodium silicate
8.0% - Moisture
0.8% - Optical brightener
0.5% - Carboxymethylcellulose Measured quantities of sodium perborate tetrahydrate were added to each vessel to provide the desired quantity of active oxygen (A.O.) followed by an amount of activator compound to give the bleaching A.O. levels. In each test run, the activator was excluded from at least one Terg-O-Tometer vessel. The pH of each solution was adjusted to about 10.0 with sodium hydroxide. The Terg-O-Tometer was operated at 100 cycles per minute for 10 or 30 minutes at the desired temperature. The swatches were then removed, rinsed under cold tap water and dried in a household clothing drier. Reflectance readings were taken on each swatch and percent tea stain removal (%TSR) was calculated as follows:

$$\% \ TSR = \frac{\text{(Reflectance After Bleaching)} - \text{(Reflectance Before Bleaching)}}{\text{(Reflectance Before Staining)} - \text{(Reflectance Before Bleaching)}} \times 100$$

The increase of %TSR, termed Δ%TSR, was calculated by subtracting the average %TSR in runs where the perborate was present alone, from the average %TSR obtained in runs where both the activator and the perborate were present.

EXAMPLE 1

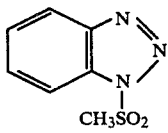

Equimolar portions (0.059 m) of sodium hydride and benzotriazole were combined in 225 ml of dry dioxane during 15 minutes. An equivalent of methanesulfonyl chloride was added and the mixture was stirred over night at ambient temperature. The reaction mixture was poured onto water, and the product isolated by filtration, yielding 7.6 grams (66%) of a white solid mp 105°–107.5° C. (lit. mp 110°–112° C.).

NMR (CDCl$_3$) δ 8.2−7.2 (m, 4H) 3.48(s, 1H) Reference for mp- S. Beveridge and J. L. Huppatz, Aust. J. Chem., 25, 1341 (1972). Stain removal tests showed % TSR values of 68 on cotton and 33 on blend using a bleaching solution that delivered 60 parts per million active oxygen with a 1:1 mole ratio of activator to perborate. The Δ% TSR values were 28 on cotton and 14 on blend. The pH was 9.6. It can be seen that methanesulfonyl benzotriazole is a good peroxygen activator.

EXAMPLE 2

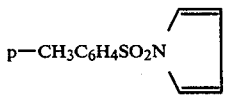

Equimolar portions (0.037 m) of sodium hydride and pyrole were combined in 70 ml of dry dioxane and stirred at about 50° C. for one hour. An equivalent of p-toluene-sulfonyl chloride was added and the mixture stirred over night at room temperature and an additional 6 hours at 50° C. The mixture was then carefully poured onto water and the product filtered and recrystallized from cyclohexane to produce a 48% yield of the desired product, mp 94°–97° C., lit. mp 100°–101° C. (ethanol)

NMR (CDCl$_3$) δ 7.7 (d, 2H) 7.3−7.0 (m, 4H) 6.2 (m, 2H) 2.4 (s, 3H)

Reference for mp - J. W. F. Wasley and K. Chan, Synthetic Communications, 3, 303 (1973). Stain removal tests show %TSR values of 62 on cotton and 31 on blend using a bleaching solution that delivered 60 parts per million active oxygen with a 0.75 activator to perborate mole ratio. The Δ%TSR values were 46 and 22 respectively, the pH was 10.3. It can be seen that p-toluenesulfonyl pyrrole is a good peroxygen activator.

We claim:

1. A process for the low temperature bleaching of stained and/or soiled fabrics characterized by treating them with an aqueous peroxygen bleaching solution having a pH of 6 to 12 and containing as a peroxygen activator therefor, an activating amount of a N-sulfonylazole of the formula

where Z represents the number of carbon and nitrogen atoms necessary to complete a heterocyclic ring selected from the class consisting of pyrazole, pyrrole, triazole and benzotriazole wherein said ring can be substituted with phenyl, alkyl of 1 to 10 carbon atoms, halogen, amino, cyano, nitro, alkoxy of 1 to 10 carbon atoms and R is an alkyl radical of 1 to 10 carbon atoms.

2. The process according to claim 1 characterized in that the mole ratio of peroxygen to activator is from 20:1 to 1:3.

3. The process according to claim 2 characterized in that the peroxygen is sodium perborate tetrahydrate.

4. The process according to claim 2 characterized in that the quantity of peroxygen is sufficient to provide from 2 parts per million to 2000 parts per million of active oxygen.

5. The process according to claim 1 characterized in that the bleach solution contains a detergent agent.

6. The process according to claim 1 characterized in that the pH of the bleach solution is maintained by means of a buffering agent.

* * * * *

UNITED STATES PATENT AND TRADEMARK OFFICE
CERTIFICATE OF CORRECTION

PATENT NO. : 4,207,070

DATED : June 10, 1980

INVENTOR(S) : Joseph H. Finley, Gaylen R. Brubaker and Burton M. Baum

It is certified that error appears in the above-identified patent and that said Letters Patent are hereby corrected as shown below:

Abstract, formula " 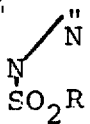 " should read -- 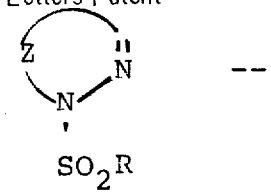 --

Column 1, line 11, "ajuncts" should read --adjuncts--. Column 2, line 38, formula, " 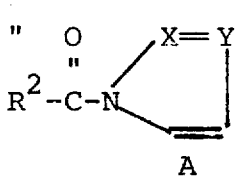 should read -- 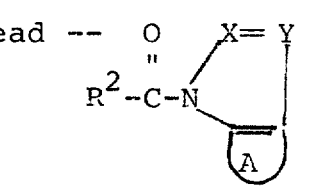 -- line 60, "clevage" should read --cleavage--. Column 3, line 47, formula " 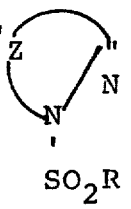 " should read -- 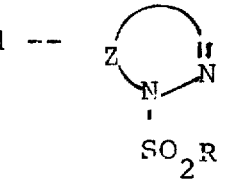 --. Column 4, line 5, formula, " 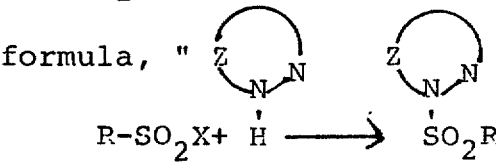 " should read $$R\text{-}SO_2X + H \longrightarrow SO_2R + HX$$

UNITED STATES PATENT AND TRADEMARK OFFICE
CERTIFICATE OF CORRECTION

PATENT NO. : 4,207,070

DATED : June 10, 1980

INVENTOR(S) : Joseph H. Finley, Gaylen R. Brubaker and Burton M. Baum

It is certified that error appears in the above-identified patent and that said Letters Patent are hereby corrected as shown below:

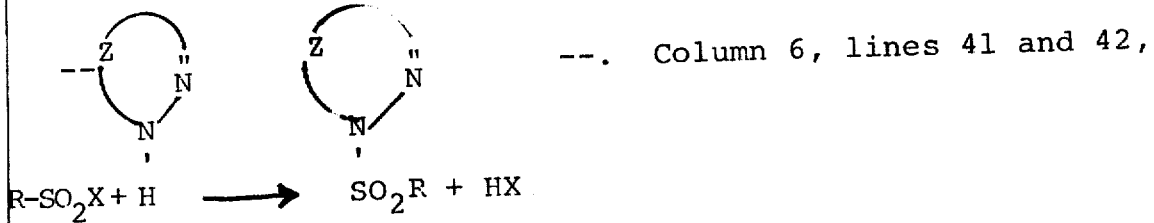

--. Column 6, lines 41 and 42, "isethionates" should read ---isoethionates---. Column 7, line 41, formula "COCH" should read --COOH--; line 48, formula "COCH" should read --COOH--. Column 12, claim 1, line 24, formula " " should read -- --.

Signed and Sealed this

Fourteenth Day of October 1980

[SEAL]

Attest:

SIDNEY A. DIAMOND

Attesting Officer — Commissioner of Patents and Trademarks